United States Patent [19]
Graham et al.

[11] Patent Number: 4,625,056

[45] Date of Patent: Nov. 25, 1986

[54] PROCESS FOR PRODUCING BENZENE CARBOXYLIC ACIDS FROM AROMATIC MATERIAL UTILIZING AN ALIPHATIC ORGANIC ACID AGENT

[75] Inventors: James R. Graham, Fountain Valley, Calif.; John G. Huntington, Arvada, Colo.

[73] Assignee: Occidental Research Corporation, Los Angeles, Calif.

[21] Appl. No.: 105,355

[22] Filed: Dec. 19, 1979

[51] Int. Cl.$^4$ .............................................. C07C 51/16
[52] U.S. Cl. ..................................... 562/407; 562/417
[58] Field of Search ................................ 562/407, 417

[56] References Cited

U.S. PATENT DOCUMENTS

| | | | |
|---|---|---|---|
| 2,245,528 | 6/1941 | Loder | 562/417 |
| 2,786,074 | 3/1957 | Goren | 562/407 |
| 3,505,397 | 4/1970 | Patten | 562/417 |
| 3,708,531 | 1/1973 | Croce | 562/417 |

*Primary Examiner*—Alan Siegel
*Attorney, Agent, or Firm*—F. Eugene Logan; William N. Patrick

[57] ABSTRACT

This invention relates to a method of producing benzene carboxylic acids from an aromatic material, especially coal, by the oxidation of the aromatic material in an aqueous alkaline mixture containing an aliphatic organic acid promoter agent with a source of gaseous oxygen. Use of the aliphatic organic acid promoter agent results in a surprising and unexpected increase in the benzene carboxylic acid yield which is higher than that obtained without the promoter agent.

A finely divided coal, potassium carbonate, water, and aliphatic carboxylic acid promoter agent are charged to a feed tank (10) where they are mixed with an agitator (14). A slurry pump (18) pumps the mixture through a preheater (20) to an autoclave (30). Air is continuously fed to the autoclave (30) by a gas compressor (34). The coal slurry is oxidized in the autoclave (30) while being agitated by a mixer (36). Gaseous products, and in particular carbon dioxide, is continuously removed from the autoclave (30) through a vent conduit (42). Benzene carboxylic acid salts produced in the autoclave (30) are removed and cooled in a cooler (52) and stored in a product tank (54).

28 Claims, 2 Drawing Figures

PROCESS FOR PRODUCING BENZENE CARBOXYLIC ACIDS FROM AROMATIC MATERIAL UTILIZING AN ALIPHATIC ORGANIC ACID AGENT

TECHNICAL FIELD

The technical field of the invention relates to the production of benzene carboxylic acids from aromatic materials, such as, but not limited to, coal, petroleum, petroleum residuum, pitch, tar, shale oil, and tar sands. The invention is particularly useful for the production of benzene carboxylic acids such as terephthalic acid from bituminous coal.

BACKGROUND ART

U.S. Pat. No. 2,785,198 discloses a process for producing polycarboxylic acids from bituminous coal, lignites, peat and the like or their carbonization products such as coal, tar, or pitch by thermal treatment with oxidizing agents such as nitric acid, chromic acid, permanganate, or oxygen or air under super-atmospheric pressure in an alkaline medium. The alkaline medium disclosed is sodium hydroxide.

The crude oxidation product is subject to an extraction treatment with a polar organic solvent for both the monocyclic aromatic and high molecular weight polycarboxylic acids, and treating the thusly formed solution with water to extract the monocyclic aromatic polycarboxylic acids from the remainder of the mixture.

U.S. Pat. No. 2,193,337 discloses a process for producing organic acids by heating carbonaceous material such as sawdust, wood chips, peat, or coal with oxygen-containing gases at elevated pressures and temperatures in the presence of at least 10 times the weight of the carbonaceous material of water and preferably an oxide or hydroxide of an alkali or alkaline earth metal. Oxalic acid and other organic acids which are formed, such as mellitic and benzoic acid or acetic acid, may be isolated from the resulting reaction mixture as salts of the alkali or alkaline earth metals. The caustic material disclosed is an oxide or hydroxide of an alkali metal or an alkaline earth metal and specifically lime, quick-lime, and caustic soda.

U.S. Pat. No. 2,786,074 discloses a process for making organic acids by oxidizing carbonaceous materials at elevated temperatures and pressures with gaseous oxygen in the presence of an alkaline solution. Alkalis which are suitable for use in a high pressure reactor are specified as sodium hydroxide, potassium hydroxide, and mixtures thereof.

U.S. Pat. No. 2,461,740 discloses a process for oxidizing carbonaceous material to aromatic acids using a two-stage oxidation process. In the first stage, the carbonaceous material is oxidized to a state where it is soluble in aqueous alkali such, for example, as a solution of sodium hydroxide, potassium hydroxide, sodium carbonate, or potassium carbonate, especially at elevated temperatures.

Any acid or acid anhydride with suitable oxidizing properties which can be regenerated by air and recycled in the process can be employed, for example, sulfur trioxide, oxides of nitrogen, or the acids formed by reaction of these compounds with water. Specifically disclosed are sulfur trioxide, $N_2O_3$, and $N_2O_5$.

In the second stage, U.S. Pat. No. 2,461,740 discloses the use of a high pressure elevated temperature reaction of oxygen gas in aqueous alkali. The aqueous alkali employed is a solution of sodium hydroxide, potassium hydroxide, sodium carbonate, or potassium carbonate.

U.S. Pat. No. 3,023,217 discloses a process for introducing carboxyl groups into aromatic compounds free from carboxyl groups, such as aromatic carbocyclic hydrocarbons and aromatic heterocyclic hydrocarbons. The patent discloses a process for introducing into aromatic carbocyclic or aromatic heterocyclic compounds free from carboxyl groups by reacting such materials in the absence of substantial amounts of oxygen, such as a non-oxidative atmosphere and under anhydrous conditions, with alkali metal salts of aliphatic carboxylic acids at elevated temperatures and pressures in the presence of catalysts. As disclosed in the process, it is necessary to exclude the presence of substantial quantities of oxygen. Examples of aliphatic carboxylic acids which are used in the form of their alkali metal salts, especially their potassium salts, are oxalic acid, malonic acid, maleic acid, and trichloroacetic acid.

Examples of suitable compounds free from carboxyl groups which may be used as starting materials for the process are aromatic carbocyclic compounds free from carboxyl groups such as monocyclic aromatic hydrocarbons such as benzene or its derivatives having saturated alkyl or cycloalkyl substitutes attached thereto, and dicyclic aromatic hydrocarbons such as naphthalenes, diphenyl, and other polycyclic aromatic hydrocarbon compounds. Similarly, aromatic heterocyclic compounds free from carboxyl groups which may be used as starting materials are heterocyclic compounds which contain one or more heteroatoms in the ring and which are designated as having an aromatic character because of their chemical behavior.

U.S. Pat. No. 2,948,750 discloses a process for carboxylating aromatic hydrocarbons by direct introduction of carbon dioxide to produce polycarboxylic acids.

Suitable starting materials which are disclosed are aromatic hydrocarbons, especially benzene but also toluene, xylene, cumene and diisopropyl benzene and other benzenes substituted with saturated or unsaturated alkyl or cycloalkyl radicals, naphthalene, diphenyl, diphenylmethane and other aromatic compounds which may also be substituted with hydrocarbon radicals.

Selective carboxylation is accomplished by heating the starting materials in the presence of an acid-binding agent, and carbon dioxide under anhydrous conditions. Examples of the acid-binding agent are carbonates of alkali metals, especially potassium carbonate, the salts of other weak acids such as bicarbonates, formates, or oxalates. Similarly, the corresponding compounds of other metals are suitable; for example, the carbonates of the alkali earth metals.

U.S. Pat. No. 3,023,216 discloses a method of introducing carboxyl groups into aromatic carbocyclic compounds free from carboxyl groups by reacting these compounds in a non-oxidative atmosphere with alkali metal salts of aromatic carbocyclic or aromatic heterocyclic carboxylic acids.

Suitable compounds which are free from carboxyl groups which may be used as starting compounds in this patent are similar to the starting compounds in U.S. Pat. No. 2,948,750.

U.S. Pat. No. 3,023,216 discloses reacting aromatic carboxylic compounds free from carboxyl groups with aromatic carboxylic acids in the form of their alkali metal salts.

Both U.S. Pat. Nos. 3,023,216 and 2,948,750 require specific chemical compounds as starting materials. U.S Pat. No. 2,833,816 discloses a process for oxidizing aromatic compounds using a catalyst comprising a lower aliphatic carboxylate salt of a heavy metal and bromine. Examples of a heavy metal are manganese, cobalt, nickel, chromium, vanadium, molybdenum, tungsten, tin, and cerium.

The metals may be supplied in the form of metal salts; for example such as manganese acetate. The bromine may be supplied as ionic bromine, or other bromine compounds soluble in the reaction medium such as potassium bromate.

Thus, the process requires the conjoint presence of bromine and a heavy metal oxidation catalyst.

The starting material required is an aromatic compound containing one or more aliphatic substituents to produce corresponding aromatic carboxylic acids.

U.S. Pat. No. 3,064,043 discloses a process for oxidizing para-toluic acid or para-formyl toluene to produce terephthalic acid.

U.S. Pat. No. 3,064,046 discloses a process for oxidizing toluic acid or formyl toluene to produce orthophthalic acid or isophthalic acid.

Both U.S. Pat. Nos. 3,064,043 and 3,064,046 require specific starting materials to be oxidized.

U.S. Pat. No. 3,558,458 discloses a process for preparing aromatic acids by treating an alkyl aryl ketone with water at an elevated temperature in the presence of a reaction promoting agent. The reaction promoting agent may comprise an alkaline catalyst, a transition metal salt, or actinic light. Examples of an alkaline catalyst include potassium acetate, lithium acetate, rubidium acetate, and cesium acetate. The process is conducted in water at a temperature of about 200° to 400° C.

The art discloses processes for the alkaline oxidation of coal employing large amounts of chemicals relative to the amount of water soluble coal acid produced, see U.S. Pat. No. 2,786,074 and a report entitled "Production of Chemicals by Oxidation of Coal", Battelle Laboratory, Columbus, Ohio of Mar. 31, 1975. The substance of the Battelle Report is incorporated herein by reference.

Recovery of caustic soda and sodium carbonate was disclosed by Industrial and Engineering Chemistry, Volume 44 (1952), at page 2791 in an article entitled "Water-Soluble Polycarboxylic Acids by Oxidation of Coal" beginning at page 2784.

Japanese patent disclosure No. 18,365 discloses the reclamation of alkali by recrystallization and requires the consumption of one part by weight of the alkali and 1.5 parts of sulfuric acid for each two parts of coal consumed.

Non-alkaline oxidation of coal generally yields about 10 parts by weight of water soluble coal acids based on 100 parts of coal carbon consumed. Alkaline oxidation yields have been about 30 to about 42 parts per 100 parts of coal carbon consumed. Therefore, alkaline oxidation processes are favored because of the higher yield possible.

In systems like HCl/KCl, $H_2SO_4/K_2SO_4$, and $HNO_3/KNO_3$, the salts do not produce an alkali solution by hydrolysis because the acids involved are too strong. These systems over oxidize the coal and therefore result in much lower yield of coal acids.

Another disadvantage of treatment of coals with strong acids is the production of unwanted by-products by chlorination, sulfation, or nitration of the aromatic nuclei of the coal.

Coal acids have been prepared by nitric acid oxidation, U.S. Pat. Nos. 3,468,943; 3,709,931; 2,555,410; in the presence of nitrogen catalyst, U.S. Pat. No. 3,702,340; and oxidation in a non-alkaline aqueous medium, U.S. Pat. No. 3,259,650.

The caustic-oxygen treatment of coal has been described in U.S. Bureau of Mines Information Circular No. 8234 at pages 74 to 98.

In another process, U.S. Pat. No. 3,259,650 discloses the use of a non-alkaline medium and produces lower yields of water soluble coal acids.

U.S. Pat. 2,927,130 discloses a process for the recovery of alkalis and terephthalic acid from aqueous solutions containing alkali salts of terephthalic acid. Alkalis of interest are sodium, potassium and ammonium. The patent discloses that dialkali salts of terephthalic acid in aqueous solution can easily be divided into difficultly soluble monoalkali salts and alkali bicarbonate by introducing carbon dioxide into the solution, and that the difficultly soluble monoalkali salts of terephthalic acid can be hydrolyzed with water into free terephthalic acid and dialkali salts of terephthalic acid. The free terephthalic acid separates out as a solid, while the dialkali terephthalate remains in solution. U.S. Pat. No. 2,927,130 is incorporated herein by reference.

U.S. Pat. No. 2,819,300 discloses a process for oxidizing carbonaceous material with nitric acid, and then oxidizing the oxidation products produced from the nitric acid-carbonaceous material reaction with sulfuric acid to complete the oxidation to benzene carboxylic acids.

Although oxidation can be carried out in reclaimable acidic media, these processes are not as desirable because of lower yields and unwanted by-products due to chlorination, sulfation, and nitration.

The art discloses a process for preparing terephthalic acid by heating pure potassium phthalate, or pure potassium isophthalate, or pure potassium benzoate in the presence of catalyst such as cadmium, zinc and other metals, as reported in the Journal of American Chemical Society, Volume 79, pages 6005 to 6008.

The art discloses a catalytic process for preparing terephthalic acid from toluene by oxidizing toluene to benzoic acid, reacting the thusly formed benzoic acid with potassium terephthalate in a methathesis reaction to produce terephthalic acid and potassium benzoate, and heating the thusly formed potassium benzoate in the presence of a catalyst to produce potassium terephthalate and benzene by a disproportionation reaction. Terephthalic acid and benzene are recovered and the thus formed potassium terephthalate is recycled to the methathesis reaction. The process is reviewed in Stanford Research Institute Report No. PEP'76-2-3 of February, 1977.

U.S. Pat. No. 3,215,735 discloses a process for treating a solution containing dialkali terephthalate and non-terephthalic acid as impurities with a reagent to adjust the pH of the solution so that terephthalic acid is in a soluble form while essentially all of the non-terephthalic acid is in an insoluble filterable form.

U.S. Pat. No. 3,579,572 discloses a process for the production of terephthalic acid which comprises treating an aqueous lithium or magnesium terephthalate solution with carbon dioxide under pressure, at a temperature between its solidification temperature and 80°

C., and separating the terephthalic acid which precipitates.

U.S. Pat. No. 3,766,258 discloses a process for the catalytic carboxylation of an alkali metal aromatic carboxylate to an acid containing at least one more carboxyl group.

U.S. Pat. No. 2,171,871 discloses that alkali metal derivatives of organic acid salts may be reacted with various reagents reactive with alkali metal organic compounds, e.g. carbon dioxide, sulfur dioxide or organic halides, to produce valuable products.

U.S. Pat. No. 2,176,348 discloses a process for preparing mellitic acid by a two-step oxidation of coal. The coal is first treated with a suitable oxidizing acid with or without the presence of a catalyst, followed by oxidation with an oxidizing salt such as alkaline permanganate.

U.S. Pat. No. 2,762,840 discloses that polycarboxy aromatic acids can be prepared by controlled oxidation with oxygen gas of an aqueous, alkaline suspension of bituminous coal.

U.S. Pat. No. 2,981,751 is directed toward a process for the oxidation of substituted aromatic compounds having at least one aliphatic, cycloaliphatic or partially oxidized aliphatic or cycloaliphatic substituent attached to the aromatic nucleus in the presence of an oxygen-containing gas and a calcined solid oxidation catalyst.

The substituted aromatic feed materials disclosed are toluene, butylbenzene, xylene, cumene, durene, dibutylbenzene, acetophenone, propiophenone, benzaldehyde, tolualdehyde, Tetralin, para-xylene, acetophenone, and cumene hydroperoxide. The oxidation is in the presence of a calcined solid oxidation catalyst which is derived by calcining an inorganic base having deposited thereon catalytic amounts of a promoting metal component.

U.S. Pat. No. 3,529,020 discloses a process for oxidizing an organic material in the presence of a heavy metal crystalline aluminosilicate having uniform pores sufficiently large to permit entry of at least a portion of the organic material, and an oxidation initiator which is present in the pores. The heavy metal crystalline aluminosilicate acts as a catalyst.

This invention is a process for producing benzene carboxylic acid salts by treating a mixture of an aromatic material, water, a water soluble reagent comprising a Group Ia or IIa metal, the reagent producing an alkaline solution by hydrolysis, and an aliphatic organic acid promoter agent, with oxygen under conditions sufficient to convert at least a portion of the aromatic material to a benzene carboxylic acid salt of the reagent. In one embodiment the aliphatic organic acid promoter has the property of increasing the yield of benzene carboxylic acid salt produced from the aromatic material by an amount which is substantially higher than that produced in its absence. The thusly formed benzene carboxylic acid salt is then recovered from the mixture or further processed into more valuable products such as by isomerization to terephthalic acid.

SUMMARY AND DISCLOSURE OF THE INVENTION

This invention increases the yield of benzene carboxylic acids, hereinafter referred to as "BCA", produced from the oxidation of a mixture of an aromatic material, water, a water soluble reagent which produces an alkaline solution by hydrolysis, and an aliphatic organic acid promoter agent. By benzene carboxylic acid or "BCA" we mean herein any one of or any mixture of benzoic; 1,2 benzene dicarboxylic; 1,3 benzene dicarboxylic; 1,4 benzene dicarboxylic; 1,2,3 benzene tricarboxylic; 1,2,4 benzene tricarboxylic; 1,3,5 benzene tricarboxylic; 1,2,3,4 benzene tetracarboxylic; 1,2,3,5 benzene tetracarboxylic; 1,2,4,5 benzene tetracarboxylic; benzene pentacarboxylic; or benzene hexacarboxylic acid. In other words, by benzene carboxylic acid or BCA as used herein and claimed we mean a benzene ring with one or more carboxyl groups attached directly to a ring carbon and containing no substituted group or groups.

The aromatic material can be coal of any grade such as bituminous, subbituminous or anthracite, lignite, peat, coke, char, petroleum, petroleum fractions such as petroleum residuum, tar, pitch, oil shale, oil from oil shale and any other material containing or capable of evolving or producing aromatic material, either liquid or solid. Coals, petroleum, petroleum residuum, tar, pitch, and oil from oil shale are preferred aromatic feed material because such material will produce a good yield of BCA by this invention.

Bituminous coal is especially preferred because of the very high yield of BCA produced by this process. Whereas, anthracitic coals because of their high aromaticity produce a high percentage of polynuclear aromatic acids. Similarly, yields from lignites are low because the oxidation of lignite produces little aromatic material, and therefore the yield of BCA is low.

The water soluble reagent comprises a Group Ia or IIa metal which produces an alkaline solution by hydrolysis. Thus, hydrogen is excluded from the group comprising Group Ia or IIa metals. The water soluble reagents which comprise Group Ia metals are preferred over those which comprise Group IIa metals because they are more reactive, and have a higher rate of reaction in this invention, and produce a higher yield of BCA.

A water soluble reagent such as potassium carbonate is especially preferred because it gives a higher yield in this invention, it is economical and may be regenerated as set forth in the preferred embodiment below. Other examples of water soluble reagents which may be used are potassium carbonate, sodium carbonate, magnesium carbonate, lithium carbonate, calcium carbonate, potassium acetate, potassium formate, potassium propionate, sodium acetate, sodium formate, sodium propionate, lithium acetate, lithium formate, lithium propionate, magnesium acetate, calcium acetate, barium acetate, beryllium acetate, etc.

Pure water in the mixture to be oxidized is not required and in fact process water may be used over and over at least in part.

The addition of an aliphatic organic acid promoter agent to the mixture increases the yield of BCA. While we do not wish to be bound by theory, it is believed that the aliphatic organic acid promoter agent controls the oxidation of the feed aromatic material by providing a free radical which serves as a chain transfer agent for the oxidation reaction, thereby speeding up the rate of oxidation and simultaneously controlling the oxidation process so as to increase the yield of BCA while reducing the conversion of the feed aromatic material to carbon dioxide.

While we usually refer to the promoter agent as an aliphatic organic acid, it is to be understood that the anhydride or the salt of such aliphatic organic acid will also work. In fact it will be readily understood that the aliphatic organic acid promoter agents and their anhydrides are converted to their salts in the oxidation zone because of the presence of the water soluble alkaline reagent. Therefore, when we refer to and claim herein an aliphatic organic acid used as promoter we mean to include its salt and its anhydride. Similarly, when we refer to and claim herein a promoter having a carboxyl group, we mean to include its salt or its anhydride. By aliphatic organic acid we mean herein and as claimed an organic acid having a carboxyl group attached directly to an aliphatic group.

The amount of the aliphatic organic acid or a salt thereof used as a promoter agent must be sufficient for and effective in increasing the yield of BCA produced from the aromatic material.

For example, the aliphatic organic acid promoter agent can contain only one carboxyl group and no substituted group such as for example vinylacetic acid. In one embodiment of this invention the aliphatic organic acid can contain only one carboxyl group and a substituted aromatic group such as for example phenylacetic acid, hydrocinnamic acid, phenylbutyric acid, phenylvaleric acid, naphthylacetic acid, diphenylacetic acid, and tolylacetic acid. In a further embodiment of this invention the aliphatic organic acid promoter agent can contain two or more carboxyl groups and an aromatic substituted group. Examples of such promoter agents are phenylmalonic acid, phenylsuccinic acid, benzylmalonic acid, and diphenylsuccinic acid. In still another embodiment the carboxyl groups may be separated by the substituted aromatic group as in for example 1,4 benzenepropanoic acid. In a still further embodiment the aromatic group may contain a substituted hetero group such as in for example chlorophenylacetic acid.

In another embodiment of this invention, the aliphatic organic acid promoter agent can contain only one carboxyl group and a substituted ether group such as for example methoxyacetic acid, ethoxyacetic acid, ethoxypropionic acid, and diglycolic acid.

In still another embodiment of this invention the aliphatic organic acid promoter agent can contain only one carboxyl group and a substituted carbonyl or keto group. Examples of such a promoter are 2-ketobutyric acid; 1,3-acetonedicarboxylic acid; 4-acetylbutyric acid; and 4--keptopimelic acid.

In still another embodiment of this invention the aliphatic organic acid promoter agent can contain only one carboxyl group and a substituted hydroxyl group such as for example glycolic acid and lactic acid. In a further embodiment the aliphatic organic acid promoter agent can contain two or more carboxyl groups and a substituted hydroxyl group such as for example malic acid. In a still further embodiment the promoter agent can contain two or more carboxyl groups and two or more hydroxyl groups such as tartaric acid, mucic acid, and citric acid.

In still another embodiment of this invention the aliphatic organic acid promoter agent can contain only one carboxyl group and two different substituted groups. For example one of the substituted groups may be aromatic and the other hydroxyl such as for example mandellic acid, tropic acid and phenyllactic acid. In another embodiment the first substituted group can be aromatic and the second substituted group an ether such as for example phenoxyacetic acid, phenoxypropionic acid, phenoxybutyric acid, phenoxyundecanoic acid, methoxyphenylacetic acid and trimethoxyphenylacetic acid. In a still further embodiment of this invention the aromatic group may contain a substituted hetero group such as for example chlorophenoxyacetic acid. In a still further embodiment of this invention the aliphatic organic acid promoter agent can contain only one carboxyl group and several hydroxyl groups as a first substituted group and several ether groups as a second substituted group. An example of such a promoter agent is lactobionic acid. In still another embodiment of this invention the aliphatic organic acid promoter agent can contain only one carboxyl group and a substituted thio group and a substituted aromatic group such as for example thiophenoxyacetic acid and benzylthioglycolic acid.

In a preferred embodiment of this invention the aliphatic organic acid promoter or a salt thereof is at least partially converted into a benzenecarboxylic acid salt or BCA salt.

In general the aliphatic organic acid promoter agent contains an aliphatic group which contains a carbonhydrogen bond in which the hydrogen thereof is easily abstracted by a radical.

In all cases the aliphatic organic acid promoter agent may be in its salt form such as its Group Ia or IIa metal salt or in such other modified forms such as ammonium or tetraalkylammonium and other derivative forms thereof as to not nullify its promoting characteristic for increasing the yield of BCA from aromatic material oxidation.

It is preferable that the aliphatic organic acid promoter agent be soluble in the alkaline solution used in the oxidation zone. It is especially preferable that the promoter agent be completely soluble in the quantity in which it is used in the oxidation zone. It is also preferred that the promoter agent have a boiling point of about 300° C. or higher in order to prevent appreciable vaporization of the promoter agent in the oxidation zone. It is also preferred that the promoter agent have a plurality of reactive sites, that is, aliphatic groups and/or substituted groups, such as aromatic groups or hydroxyl groups, in its chemical structure.

It is also preferred that the promoter agent have surfactant properties, be stable in that it has a good shelf life, and be non-toxic for industrial hygiene purposes.

Preferably about 1 to about 50 parts by weight of water per part by weight of feed aromatic material, about 1 to about 30 parts by weight of a water soluble reagent comprising a Group Ia or IIa metal per part by weight of feed aromatic material, and about 0.01 to about 1 part by weight of an aliphatic organic acid promoter agent per part by weight of feed aromatic material are used in preparing the slurry. Preferably enough water is used to enable the slurry to be pumped. Preferably enough water soluble reagent is used to supply the stoichiometric requirements of the reaction.

The mixture can be formed in any manner in a mixing zone using mixers suitable for handling slurries containing solids if a solid or solid-like carbonaceous material is used to produce BCA, or mixers suitable for handling liquids if liquid aromatic materials are to be used to produce BCA.

The mixture is removed from the mixing zone and fed to a reaction zone wherein the mixture is reacted with oxygen, or an oxygen-containing gas such as air. The reaction zone and the mixing zone can be, if desired, in the same vessel as in some batch-type processes, or they may be separate vessels as in some continuous processes. However, a continuous process for the oxidation of the aromatic feed material is preferred over a batch system not only because of process efficiency but also because yields appear to be higher.

The mixture is treated with oxygen under conditions sufficient to convert at least a portion of the aromatic material into a BCA salt of the reagent. In general, a temperature of about 200 to about 350° C. is required. The pressure in the reaction zone should be sufficient to maintain a liquid state in the reaction zone. Generally this requires a pressure of at least about 250 psig ($17.2 \cdot 10^6$ dynes/cm$^2$). Preferred reaction zone conditions are about 270° C. and about 900 psig ($62.1 \cdot 10^6$ dynes/cm$^2$).

Reaction times in the reaction zone depend upon the temperature, degree of agitation, the proportion of feed aromatic material, water, and water soluble reagent, the solid-to-liquid ratio, and the particle size of the solid material. Generally, reaction times of from about ten minutes to about three hours are required.

During oxidation BCA is formed which reacts with the reagent to form BCA salts, and carbon dioxide or the volatile acid of the reagent, all of which can be reclaimed by recycling directly or venting the vapor from the reactor and condensing.

The BCA salts can be separated from the mixture by evaporation and drying or by other means. The separated BCA salts can be recovered or further treated, for example, as by isomerizing to produce terephthalic acid salt which can be further treated for production and recovery of terephthalic acid.

Alternately, the BCA salts while in solution can be converted to BCA by treatment of the BCA salt solution from the oxidation zone with an acid. The acid of the BCA salts, or BCA, is caused to precipitate at least in part by the aforementioned treatment. The precipitate BCA is then recovered from the aqueous slurry.

For example, in one embodiment of this invention, after treating the mixture with oxygen or an oxygen-containing gas such as air to produce BCA salts, water is removed from the mixture in a dewatering zone. In the dewatering zone, an amount of water is removed which is sufficient that upon the addition of "an acid of said reagent" that at least a portion of the BCA salt will be converted to an aromatic carboxylic acid precipitate. The solution will contain the regenerated reagent which can be recycled for further use.

As used above and hereinafter, the expression "an acid of the reagent" means an acid which is formed by the replacement of the Group Ia or IIa metal atom of the water soluble reagent with hydrogen.

The dewatering zone can be in the same vessel as the reaction zone as in some batch processes, or it can be in a separate vessel as in some continuous processes.

The water from the dewatering zone can be used in the mixing zone to supply at least part of the water requirements for the mixing zone.

The dewatered mixture, i.e., the mixture from the dewatering zone, is then treated in an acidification zone with an acid of the reagent to convert the BCA salt to an aromatic carboxylic acid precipitate and the reagent. For example, potassium terephthalate treated with carbonic acid or with carbon dioxide is converted to potassium hydrogen terephthalic and potassium bicarbonate.

The acidification zone may be in the same vessel as the dewatering zone as in some batch processes, or it can be in a separate acidification vessel as in some continuous processes. Sufficient acid is added in this embodiment to the mixture to effect the conversion of the BCA salt to BCA and to cause precipitation.

After forming the BCA precipitate, the precipitate is separated from the mixture in a separation zone. Any apparatus capable of separating solids from liquids may be used such as a filter. The separated solid comprises the BCA precipitate.

In one embodiment of the invention, the separated liquid from the separation zone is treated in a regeneration zone to recover the reagent from the liquid. The liquid stream from the acidification zone contains both the reagent and an acid of the reagent. The reagent and the acid of the reagent are separated in a separation zone. The separated reagent can be used for additional treatment of fresh aromatic material in the mixing zone whether the process is batch or continuous. The separated acid of the reagent can be used to acidify additional material in the acidification zone whether the process is batch or continuous.

In another embodiment of this invention, terephthalic acid is produced by drying the BCA salt produced from the feed aromatic material and heating the dry BCA under isomerization conditions of elevated temperature and pressure to produce terephthalic acid salt. In one embodiment, isomerization is performed without converting the BCA salt to a BCA salt of a different Group Ia or IIa metal prior to isomerizing the BCA salt. Thus, for example, in this particular embodiment, a sodium salt of BCA is not converted to a potassium salt of BCA prior to isomerization, thereby saving the step of converting sodium BCA to potassium BCA prior to isomerization and associated cost.

The terephthalic acid salt thusly produced is then converted to a terephthalic acid, and the reagent comprising said Group Ia or IIa metal is regenerated. Terephthalic acid is recovered and the reagent comprising the Group Ia or IIa metal thusly regenerated is recycled to the oxidation zone to supply a portion of the reagent required for producing the BCA salt.

The process is particularly valuable where the feed aromatic material is coal, the reagent is a potassium carbonate, and the aliphatic organic acid promoter agent is tolylacetic acid.

BEST MODE FOR CARRYING OUT THE INVENTION

Figure 1:
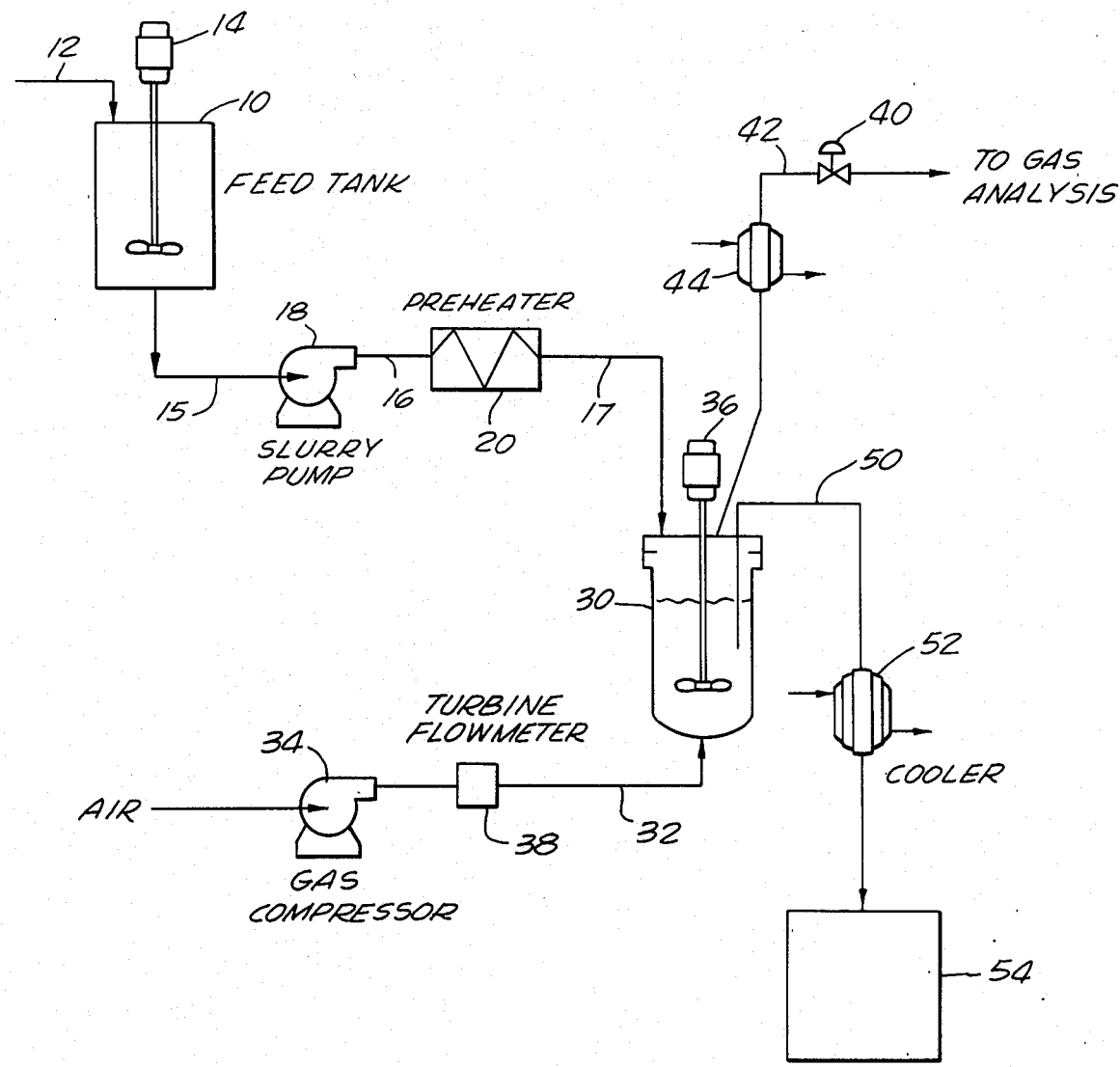
FIG. 1 is a schematic flow diagram of the continuous coal oxidation unit.

Referring to FIG. 1, which is a schematic diagram of a continuous coal oxidation unit, hereinafter referred to as "CCOU", a coals slurry consisting of 3 percent finely divided coal, 9 percent potassium carbonate, 0.1 part tolylacetic acid as an aliphatic organic acid promoter agent for every part of coal, and the balance water is added to slurry feed tank 10 through conduit 12. The coal, potassium carbonate, tolylacetic acid and water are mixed in tank 10 with mixer 14. The mixed slurry is pumped at a rate of 0.1 kilograms per minute from tank 10 through conduits 15, 16 and 17 by pump 18. The slurry is heated to a temperature of about 225° C. in preheater 20 which is spaced between conduits 16 and 17. The preheated slurry enters autoclave 30 through conduit 17 where it is treated with air entering through conduit 32 which is forced into autoclave 30 by gas compressor 34. The slurry is treated with air over a period of 60 minutes while being agitated by mixer 36. Turbine flow meter 38 measures the flow of air into autoclave 30. The flow of air is controlled by a control valve which is not shown. About 3 grams of oxygen per gram of moisture and ash-free coal, hereinafter referred to as "MAF coal", are used to oxidize the coal and produce BCA salts. The autoclave is operated at a temperature between about 270° and about 310° C., and a pressure between about 1400 and about 1600 psig (96.5 to 110 dynes $10^6/cm^2$).

The pressure in autoclave 30 is controlled by pressure control valve 40 contained in vent conduit 42. Conduit 42 also contains heat exchanger 44 which is used to cool the vent gases so that they may be sent to a gas analysis section not shown for analysis of gases such as oxygen, carbon monoxide, and carbon dioxide.

The oxidized coal slurry is continuously withdrawn from autoclave 30 through conduit 50, cooled in heat exchanger 52, and stored in product tank 54.

Figure 2:
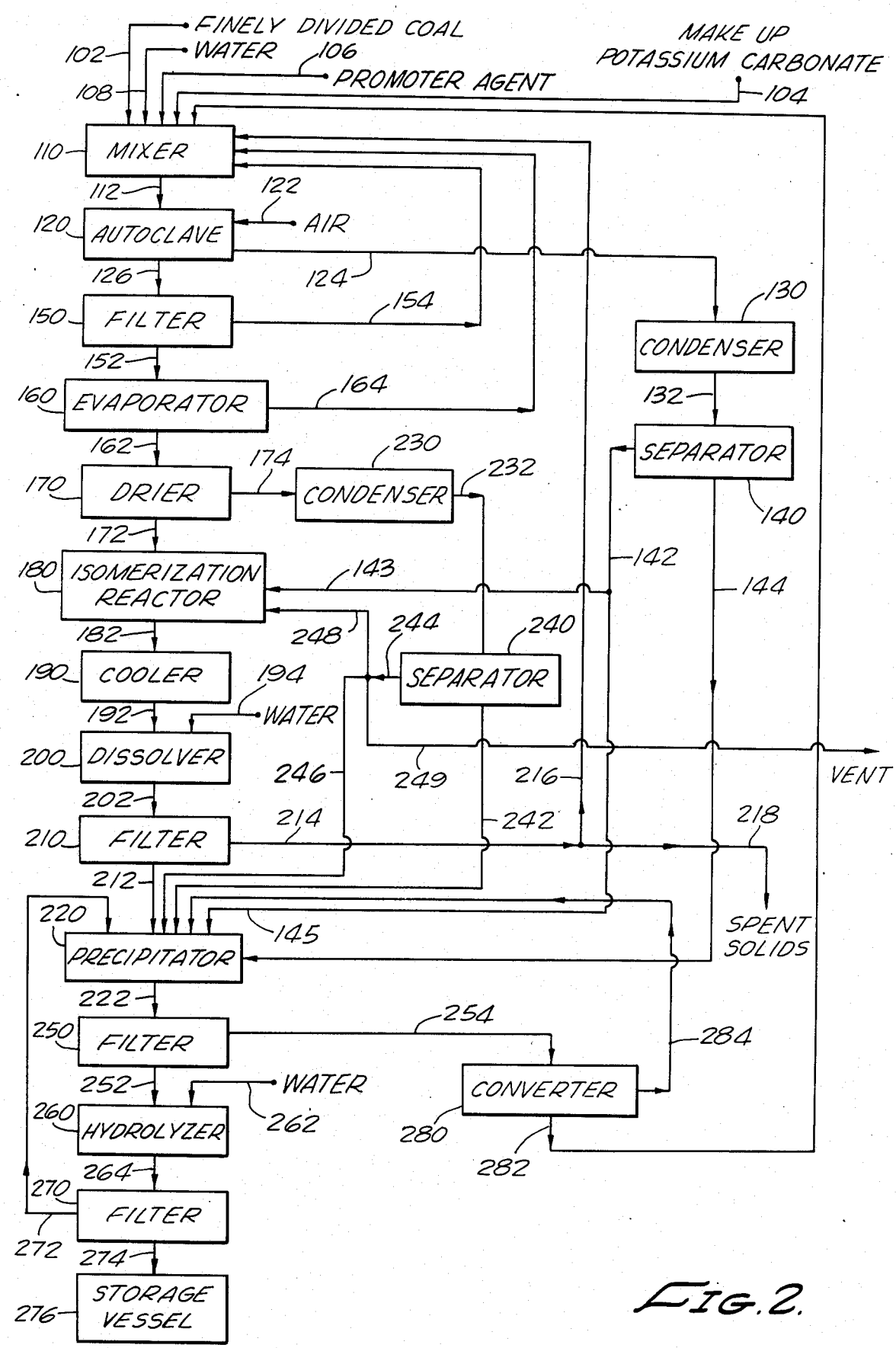
FIG. 2 is a schematic block diagram of a process for producing terephthalic acid from bituminous coal.

Referring to FIG. 2, which is a block diagram of a process for producing BCA salts from coal and the isomerization of the BCA salts to terephthalic acid such as that which can be employed in a commercial operation, a finely-divided bituminous coal through conduit 102, potassium carbonate as the alkaline water-soluble reagent through conduit 104, tolylacetic acid as the aliphatic organic acid promoter agent through conduit 106 and water through conduit 108 are introduced into mixer 110. About 2 to about 50 parts by weight of water, about 1 to about 30 parts by weight of potassium carbonate, and about 0.01 to about 1 part by weight of an aliphatic organic acid promoter agent per part by weight of coal are used in preparing the slurry. Preferably about 4 to about 8 parts by weight of water, about 2 to about 4 parts by weight of potassium carbonate, and about 0.05 to about 0.15 parts by weight of an aliphatic organic acid promoter agent per part by weight of coal are used in preparing the slurry. It is especially preferred that about 6 parts by weight of water, about 3 parts by weight of potassium carbonate, and about 0.1 part of tolylacetic acid as an aliphatic organic acid promoter agent are added to mixer 110 per part by weight of feed coal added to mixer 110. Any type of mixer may be used, although a mixer for mixing slurries containing solids is preferred.

After mixing, the mixture is removed from mixer 110 through stream 112 and introduced into autoclave 120. Air or oxygen is introduced into autoclave 120 through line 122. About 2 parts by weight of oxygen per part by weight of feed coal is charged to autoclave 120. The coal in the alkaline aqueous slurry is oxidized in autoclave 120 to produce potassium BCA salts and potassium polynuclear aromatic acid salts. Carbon dioxide and water are also simultaneously produced during the oxidation process.

Autoclave 120 is operated at a temperature of about 200° to about 350° C., preferably about 270° C., and at a pressure of about 250 to about 2000 psig (17 to 138 dynes·$10^6$ dynes per square centimeter), preferably about 900 psig (62·$10^6$ dynes per square centimeter). Temperatures below about 200° C. are not desirable because the formation of polynuclear aromatic carboxylic acids is favored over the formation of BCA, and temperatures above about 350° C. are not desirable because the formation of carbon dioxide is favored over the formation of BCA. Pressures outside this range can be used; however, lower pressures are not desirable because kinetic rates are lower and higher pressures are not desirable because of the cost of high pressure equipment and compression costs. Preferably the contents of autoclave 120 are agitated to increase product yield and to lower reaction time.

Gases comprising carbon dioxide and water vapor are removed from autoclave 120 through line 124 and fed into condenser 130, wherein water vapor is condensed and carbonic acid is formed. The condensate and remaining uncondensed gas are removed from condenser 130 through conduit 132 and fed to separator 140. The condensate comprising aqueous carbonic acid is separated from the remaining gas comprising carbon dioxide in separator 140. The gas is removed from separator 140 through conduit 142, and the condensate through conduit 144. Both streams 142 and 144 are fed to subsequent steps in the process, as will be described below.

The aromatic carboxylic acid salts, including the potassium BCA salts, are discharged from autoclave 120 through conduit 126 to filter 150. Filter 150 is used to separate the liquid product containing dissolved potassium BCA salts from residual solids. Filter 150 may be any type of filter, such as a precoated revolving drum filter or a vacuum filter. The liquid product containing the dissolved thusly formed potassium BCA salts is removed from filter 150 through conduit 152. The solids which contain unreacted coal and ash are removed from filter 150 through line 154 and recycled to mixer 110 to undergo further oxidation to produce additional aromatic carboxylic acid salts including BCA salts.

The filtration step is optional and is not needed if the solids in stream 126 will not interfere with a subsequent isomerization step as described later.

Liquid stream 152 from filter 150 is charged to evaporator 160, where most of the water therein is removed. The damp solids containing the thusly formed potassium carboxylic acid salts, including the potassium BCA salts, are removed from evaporator 160 through conduit 162 and are introduced into drier 170. Water from evaporator 160 is removed through conduit 164 and recycled to mixer 110.

In drier 170, the remaining water is removed from the damp solids thereby producing dried solids which comprise a mixture of potassium aromatic carboxylic acid salts.

However, rather than recovering potassium BCA salts from stream 172, it is desirable to use them as a precursor for the production of terephthalic acid in the embodiment as further shown in FIG. 2. Accordingly, the dry solids thusly formed are removed from drier 170 through line 172 and charged to isomerization reactor 180. It is important to dry the solids in drier 170 before introducing them to isomerization reactor 180 to a sufficient extent suitable for preventing significant reaction between any remaining water in the dry solids and the aromatic carboxylic acid salts during isomerization.

In an alternate embodiment, potassium benzoate can be introduced into isomerization reactor 180 to simultaneously undergo conversion to terephthalic acid.

In another alternate embodiment, benzoic acid can be introduced into mixer 110 or autoclave 120 to produce additional benzene dicarboxylic acid salts by a disproportiation reaction between aromatic polycarboxylic acids and the benzoic acid.

In isomerization reactor 180, the dry aromatic carboxylic acid salts, including the BCA salts, are catalytically isomerized at a temperature of from about 400° to about 440° C., at a pressure of about 10 atmospheres, for a period of time of about 10 to about 100 minutes to cause isomerization of the dry potassium aromatic carboxylic acid salts to more valuable products such as terephthalate and isomerized polynuclear aromatic carboxylic acid salts.

Preferably, a carbon dioxide environment is maintained in the isomerization reactor 180. In an especially preferred embodiment, a portion of the carbon dioxide that is produced in the oxidation step is fed to the isomerization reactor 180 through conduit 143 from conduit 142. If desired, gases other than carbon dioxide may be removed from the gases in conduit 143 before this stream is introduced into isomerization reactor 180. If free oxygen is present in stream 143, then it must be removed or converted to carbon dioxide (not shown) before the gas is fed to isomerization reactor 180. Stream 143 may be used as a source of carbon dioxide without any subsequent purification or treatment if it does not contain free oxygen, since it is not necessary to use pure carbon dioxide. In still another embodiment, any inert atmosphere such as nitrogen may be used.

Examples of catalysts useful for promoting the isomerization are the oxides, carbonates, or halides of zinc or cadmium. Organic salts, particularly carboxylates such as cadmium benzoate, are particularly good catalysts. Cadmium iodide is a preferred catalyst, in concentrations varying from 1 to 15 parts by weight per 100 parts by weight of aromatic carboxylic acid salts. The preferred concentration of cadmium iodide is about 5 parts by weight per 100 parts by weight of the aromatic carboxylic acid salt mixture.

The products are removed from isomerization reactor 180 through conduit 182 and enter cooler 190 where the products are cooled to a temperature of about 100° to about 200° C., preferably about 100° C. It is necessary to cool the products because decomposition occurs at higher temperatures when exposed to water or oxygen. For example, exposure to water can cause potassium terephthalate to decompose to benzoic acid and potassium bicarbonate; and exposure to oxygen can cause potassium terephthalate to decompose to carbon dioxide and potassium bicarbonate.

The cooled products removed from cooler 190 through conduit 192, together with water from conduit 194, are charged to dissolver 200. In dissolver 200 the potassium aromatic carboxylic acid salts including the potassium BCA salts are completely dissolved except for polynuclear aromatic carboxylic acid salts having a very high molecular weight.

The mixture is removed from dissolver 200 through conduit 202 and enters filter 210 where any undissolved solids are separated from the liquid portion of the mixture. The thusly separated liquid portion is removed from filter 210 through conduit 212 and charged to precipitator 220. If desired, the solution can be treated with activated charcoal to remove any impurities which impart a color to the terephthalic acid solution prior to the precipitation step.

The thusly separated solids, which consist essentially of char and ash, are removed from filter 210 as stream 214 and a portion thereof is recycled to mixer 110 as stream 216, or alternately the solids are recycled to autoclave 120 (not shown), to undergo further oxidation to produce additional aromatic carboxylic acid salts. In order to prevent buildup of solids, principally ash, in the system, another portion of the solids is removed from the system as stream 218.

In still another embodiment (not shown), solids from filter 210 are mechanically treated or floated to separate the ash material from the carbonaceous material. The carbonaceous material can be returned to mixer 110, or alternately to autoclave 120, while the separated ash fraction is removed from the system.

Returning to drier 170, the vapor stream, removed from the drier through conduit 174, is fed to condenser 230, whereupon water vapor is condensed. Carbonic acid will be formed in the condensate because of the presence of carbon dioxide in vapor stream 174. The condensate and gases are removed from condenser 230 through conduit 232 and fed to separator 240 which is used to separate the condensate containing carbonic acid from the gases. The separated condensate is removed from separator 240 through conduit 242 and introduced into precipitator 220 to supply at least part of the acid necessary for effecting precipitation.

Gases removed from separator 240 through conduit 244, which comprise carbon dioxide, can be used at least in part to acidify the solution in precipitator 220, as shown by their introduction into precipitator 220 through conduit 246. In this embodiment, precipitator 220 is used to precipitate the monopotassium salt of terephthalic acid by treatment with carbon dioxide. Thus, the aqueous solution containing dipotassium terephthalate in stream 212 is treated in precipitator 220 with carbon dioxide to produce the monopotassium salt of terephthalic acid and potassium bicarbonate. Precipitator 220 is maintained at a temperature below about 50° C., preferably below 30° C., and especially preferably at about 0° C. to enhance the dissolving of carbon dioxide in the solution. The carbon dioxide required in the precipitation zone can be furnished entirely from the vent gas from the isomerization reactor 180. As shown in FIG. 2, a portion of the carbon dioxide from separator 140 is introduced into precipitator 220 through conduit 145.

Stream 222, which contains the monopotassium salt of terephthalic acid as a precipitate, is removed from precipitator 220 and introduced into filter 250 to separate the aqueous solution of potassium bicarbonate from the monopotassium salt of terephthalic acid.

The separated monopotassium salt of terephthalic acid is removed from filter 250 as stream 252 and is then charged to hydrolyzer 260 where it is treated with water introduced from conduit 262 into hydrolyzer 260. In hydrolyzer 260, which is preferably operated at the boiling point of the solution, dipotassium terephthalate and terephthalic acid are formed. The thusly formed dipotassium terephthalate remains in solution while the terephthalic acid precipitates. The terephthalic acid precipitate is removed from hydrolyzer 260 in stream 264 and introduced into filter 270, whereupon the terephthalic acid is separated from the dipotassium terephthalate solution and the dipotassium terephthalate filtrate is recycled to precipitator 220 by means of conduit 272, or treated in another precipitation zone. In either case, the dipotassium terephthalate in stream 272 is treated with carbon dioxide, either in the same precipitator 220 (as shown) or in a separate precipitator (not shown), to convert the dipotassium terephthalate to monopotassium salt of terephthalic acid and additional potassium bicarbonate. Terephthalic acid as product is removed as stream 274 from filter 270 and stored in storage vessel 276.

The monopotassium salt of terephthalic acid can be neutralized by other means, if desired, such as treatment with carbon dioxide or an acid such as acetic acid in an aqueous solution.

The potassium bicarbonate filtrate is removed from filter 250 in conduit 254 and can be, in another embodiment not shown in FIG. 2, recycled to mixer 110, or alternately to autoclave 120, as the water soluble reagent comprising a Group Ia or IIa metal. In the embodiment shown in FIG. 2, however, the potassium bicarbonate is introduced into converter 280 where it is converted to potassium carbonate and carbon dioxide by heating, and the potassium carbonate is recycled to mixer 110 through conduit 282, or alternately to autoclave 120, as the water soluble reagent comprising a Group Ia or IIa metal. The carbon dioxide formed in converter 280 is removed through conduit 284 and recycled to precipitator 220, or in another embodiment to isomerization reactor 180, or vented.

It has been found that weathering the coal, especially the bituminous coal by exposing it to air at ambient conditions for an extended period of time before treating the coal in said oxidation zone increases the yield of BCA. For example coal stored in the presence of moist air for three months so that the weathering could occur increases the yield of BCA.

As can be seen in this embodiment, the alkali metal reagent, which is potassium in the above description, is recovered and recycled in the process. As can be further seen, no conversion of the potassium benzene carboxylic acid salts prior to isomerization is required in the process. That is to say, it is not necessary to convert the potassium benzene carboxylic salt or potassium BCA salt to a sodium benzene carboxylic acid salt or a sodium BCA salt, or vice versa, prior to isomerization.

The principal advantage of this process is the increase in yield of benzene carboxylic acid produced from the aqueous alkaline oxidation of aromatic material achieved by the addition of an aliphatic organic acid promoter agent to the oxidation zone.

Another advantage of this process is that it is not necessary to convert the benzene carboxylic acid salts to their benzene carboxylic acids prior to isomerization.

Still another advantage of this process is that after the aromatic material is oxidized in the presence of a compound comprising a first Group Ia or IIa metal to form a benzene carboxylic acid salt of the first Group Ia or IIa metal, it is not necessary to convert the benzene carboxylic acid salt of the first Group Ia or IIa metal to another aromatic carboxylic acid salt of a second Group Ia or IIa metal prior to isomerization.

Another advantage is that the reagent is regenerated by the process and recycled.

The process of the invention has been described generally. It will be apparent to those skilled in the art from the foregoing that various modifications of the process and the materials disclosed herein can be made without departure from the spirit of the invention.

Accordingly, the invention is not to be construed or limited to the specific embodiments illustrated, but only as defined in the following claims.

INDUSTRIAL APPLICABILITY

Benzene carboxylic acids can be used as precursors for producing more valuable chemicals such as terephthalic acid. As previously described, dry potassium benzene carboxylic acids can be isomerized to produce terephthalic acid. Terephthalic acid is useful as a precursor for producing polyesters which are useful for producing fibers for the garment industry and plastic containers for liquids and other materials in the bottle or container industry. Benzoic acid is useful as a precursor to valuable chemicals such as phenol. 1,3,5-benzenetricarboxylic acid is useful as a crosslinking agent in the polymer industry. 1,3-benzene dicarboxylic acid has been used as a monomer for polyester. Furthermore, the octyl esters of the latter two acids are useful as plasticisers.

What is claimed is:

1. A process for producing terephthalic acid from coal comprising:
   a. treating in an oxidation zone a mixture of coal, water, potassium carbonate, and an amount of an aliphatic organic acid or a salt thereof effective for increasing the yield of benzene carboxylic acid salt, with oxygen at an oxidation temperature of from about 250° to about 310° C., an oxidation pressure of from about 50 to about 140 dyens·$10^6$ per square centimeter, an average residence time of treatment with oxygen of from about 10 minutes to about 4 hours, and an amount of said aliphatic organic acid or a salt thereof of from about 0.01 to about 1 parts per part of coal, to convert said coal to a water soluble potassium benzene carboxylic acid salt, said aliphatic organic acid having a carboxyl group or salt thereof connected directly to an aliphatic group, said aliphatic organic acid increasing the yield of benzene carboxylic acid salt thusly produced from said aromatic material by an amount higher than an amount of said benzene carboxylic acid salt produced in the absence of said aliphatic organic acid or a salt thereof, thereby producing a first solution containing dissolved therein said water soluble potassium benzene carboxylic acid salt and carbon dioxide;
   b. removing a gaseous stream comprising said carbon dioxide from said oxidation zone;
   c. separating undissolved solids from said first solution to produce an essentially solids-free first solution;
   d. removing sufficient water from said essentially solids-free first solution so that said water soluble potassium benzene carboxylic acid salt can be isomerized, thereby producing a dried potassium benzene carboxylic acid salt mixture;
   e. isomerizing said dried potassium benzene carboxylic acid salt mixture by heating under an atmosphere comprising carbon dioxide to produce a dipotassium terephthalic acid salt;
   f. utilizing a first portion of said gaseous stream comprising said carbon dioxide to form said atmosphere comprising carbon dioxide in said isomerization zone;
   g. dissolving said dipotassium terephthalic acid salt in a first dipotassium terephthalate solution in a dissolving zone to produce a second dipotassium terephthalate solution;
   h. separating undissolved solids in said second dipotassium terephthalate solution from said solution, thereby producing an essentially solids-free second dipotassium terephthalate solution;
   i. treating said essentially solids-free second dipotassium terephthalate solution in a precipitation zone with carbon dioxide to produce and precipitate monopotassium terephthalate and to produce a potassium bicarbonate solution;
   j. utilizing a second portion of said gaseous stream comprising said carbon dioxide as said carbon dioxide used in said precipitation zone;

k. separating said precipitated monopotassium terephthalate from said potassium bicarbonate solution, thereby producing a separated precipitated monopotassium terephthalate and a separated potassium bicarbonate solution;

l. converting said separated potassium bicarbonate solution to a potassium carbonate solution;

m. utilizing said potassium carbonate solution as at least a portion of said potassium carbonate and said water used in said oxidation zone;

n. heating a mixture of said separated precipitated monopotassium terephthalate and water under conditions of elevated temperature sufficient to produce and precipitate terephthalic acid and to produce a third dipotassium terephthalate solution;

o. separating said precipitated terephthalic acid from said third dipotassium terephthalate solution, thereby producing a terephthalic acid product and a separated third dipotassium terephthalate solution; and p. utilizing said separated third dipotassium terephthalate solution as at least a portion of said first dipotassium terephthalate solution used in said dissolving zone.

2. The process of claim 1 wherein said coal is a bituminous coal.

3. The process of claim 1 wherein said aliphatic group contains a carbon-hydrogen bond in which the hydrogen is easily abstracted by a radical.

4. The process of claim 3 further comprising weathering said coal by exposing it to air at ambient conditions for an extended period of time before treating said coal in said oxidation zone.

5. The process of claim 1 wherein said aliphatic organic acid is tolylacetic acid.

6. The process of claim 2 wherein said aliphatic organic acid is tolylacetic acid.

7. A process for producing benzene carboxylic acid salts from an aromatic material comprising treating a mixture of an aromatic material, water, a water soluble reagent comprising a Group Ia or IIa metal, said water soluble reagent producing an alkaline solution by hydrolysis, and an effective amount of an aliphatic organic acid or a salt thereof suitable for increasing the yield of said benzene carboxylic acid salts, with oxygen under conditions sufficient to produce from said aromatic material, benzene carboxylic acid salts of said Group Ia or IIa metal of said water soluble reagent, said aliphatic organic acid or a salt thereof being an organic compound having a carboxyl group or a salt thereof connected directly to an aliphatic group, said aliphatic organic acid or a salt thereof having the property of increasing the yield of said benzene carboxylic acid salts thusly produced from said aromatic material to an amount higher than an amount of said benzene carboxylic acid salts produced in the absence of said aliphatic organic acid; heating said benzene carboxylic acid salts thusly formed form said mixture to an elevated temperature under isomerization conditions to form a terephthalic acid salt of said Group Ia or IIa metal; and recovering said terephthalic acid salt.

8. A process for producing benzene carboxylic acid salts from coal comprising treating in an oxidation zone a mixture of coal, water, a water soluble reagent comprising a Group Ia or IIa metal, said water soluble reagent producing an alkaline solution by hydrolysis, and an amount of an aliphatic organic acid or a salt thereof effective for increasing the yield of said benzene carboxylic acid salts, with oxygen at an oxidation temperature of from about 250° to about 310° C., an oxidation pressure of from about 50 to about 140 dynes·$10^6$ per square centimeter, an average residence time of treatment with oxygen of from about 10 minutes to about 4 hours, and an amount of said aliphatic organic acid or a salt thereof of from about 0.01 to about 1 parts per part of coal, to produce from said coal, benzene carboxylic acid salts of said Group Ia or IIa metal of said water soluble reagent, said aliphatic organic acid or a salt thereof being an organic compound having a carboxyl group or a salt thereof connected directly to an aliphatic group, said aliphatic organic acid or a salt thereof having the property of increasing the yield of said benzene carboxylic acid salts thusly produced from said coal to an amount higher than the conversion of said coal to benzene carboxylic acid salts in the absence of said aliphatic organic acid or a salt thereof; heating said benzene carboxylic acid salts thusly formed form said mixture to an elevated temperature under isomerization conditions to form a terephthalic acid salt of said Group Ia or IIa metal; and recovering said terephthalic acid salt.

9. A process for producing benzene carboxylic acid salts from coal comprising:

(a) weathering coal by exposing it to air at ambient conditions for an extended period of time; and (b) after said weathering, treating a mixture of said weathered coal, water, potassium carbonate, and an effective amount of an aliphatic organic acid or a salt thereof suitable for increasing the yield of said benzene carboxylic acid salts, with oxygen under conditions sufficient to produce from said coal, potassium benzene carboxylic acid salts, said aliphatic organic acid or a salt thereof being an organic compound having a carboxyl group or a salt thereof connected directly to an aliphatic group and wherein said aliphatic group contains a carbonhydrogen bond in which the hydrogen is easily abstracted by a radical, said aliphatic organic acid or a salt thereof having the property of increasing the yield of said benzene carboxylic acid salts thusly produced from said coal to an amount higher than an amount of said benzene carboxylic acid salts produced from said coal in the absence of said aliphatic organic acid; and recovering said benzene carboxylic acid salts thusly formed, from said mixture.

10. A process for producing benzene carboxylic acid salts from coal comprising:

(a) weathering coal by exposing it to air at ambient conditions for an extended period of time; and (b) after said weathering, treating a mixture of coal, water, a water soluble reagent comprising a Group Ia or IIa metal, said water soluble reagent producing an alkaline solution by hydrolysis, and an effective amount of an aliphatic organic acid or a salt thereof suitable for increasing the yield of said benzene carboxylic acid salts, with oxygen under conditions sufficient to produce from said coal, benzene carboxylic acid salts of said Group Ia or IIa metal of said water soluble reagent, said aliphatic organic acid or a salt thereof being an organic compound having a carboxyl group or a salt thereof connected directly to an aliphatic group and wherein said aliphatic group contains a carbonhydrogen bond in which the hydrogen is easily abstracted by a radical, said aliphatic organic acid or a salt thereof having the property of increasing the yield of said benzene carboxylic acid salts thusly produced from said coal to an amount higher than an amount of said benzene carboxylic acid salts produced from said coal in the absence of said aliphatic organic acid; and recovering said benzene carboxylic acid salts thusly formed, from said mixture.

11. The process of claim 9 wherein said conditions are an oxidation temperature of from about 250° to about 310° C. an oxidation pressure of from about 50 to about 140 dynes·$10^6$ per square centimeter, an average residence time of treatment with oxygen of from about 10 minutes to about 4 hours, and wherein said amount of said aliphatic organic acid or a salt thereof of is from about 0.01 to about 1 parts per part of coal.

12. The process of claim 7 or 8 wherein said water soluble reagent comprising a Group Ia or IIa metal is potassium carbonate.

13. The process of claim 7 wherein said aromatic material is selected from the group consisting of coal, petrolem. petroleum residium, pitch, tar, oil shale, and oil from oil shale.

14. The process of claim 12 wherein said aliphatic group contains a carbon-hydrogen bond in which the hydrogen is easily abstracted by a radical.

15. The process of claim 13 wherein said aliphatic group contains a carbon-hydrogen bond in which the hydrogen is easily abstracted by a radical.

16. The process of claim 14 further comprising weathering said coal by exposing it to air at ambient conditions for an extended period of time before treating said coal in said oxidation zone.

17. The process of claim 15 further comprising weathering said coal by exposing it to air at ambient conditions for an extended period of time before treating said coal in said oxidation zone.

18. The process of claim 10 or 8 wherein said coal is a bituminous coal.

19. The process of claim 7 or 8 wherein said aliphatic group contains a carbon-hydrogen bond in which the hydrogen is easily abstracted by a radical.

20. The process of claim 19 further comprising weathering said coal by exposing it to air at ambient conditions for an extended period of time before treating said coal in said oxidation zone.

21. The process of claim 9 10, 7 or 8 wherein said aliphatic organic acid is tolylacetic acid.

22. The process of claim 18 wherein said aliphatic organic acid is tolylacetic acid.

23. The process of claim 7 wherein said aromatic material is selected from the group consisting of coal, bituminous coal, coke, and char.

24. The process of claim 7 wherein the amount of said water soluble reagent is from about 1 to about 30 parts by weight per part by weight of said aromatic material.

25. The process of claim 23 wherein the amount of said water soluble reagent is from about 1 to about 30 parts by weight per part by weight of said aromatic material.

26. The process of claim 10 or 8 wherein the amount of said water soluble reagent is from about 1 to about 30 parts by weight per part by weight of said coal.

27. The process of claim 10 or 7 wherein said aliphatic organic acid or a salt thereof is at least partially converted into a benzene carboxylic acid salt.

28. The process of claim 10 or 7 wherein said aliphatic organic acid or a salt thereof has only one carboxyl group or a salt thereof in its structure.

* * * * *